United States Patent [19]
Morales

[11] Patent Number: 6,141,855
[45] Date of Patent: Nov. 7, 2000

[54] STENT CRIMPING TOOL AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 09/069,010

[22] Filed: Apr. 28, 1998

[51] Int. Cl.[7] .............................. B23P 11/00; B21D 39/00
[52] U.S. Cl. ................................ 29/516; 606/1; 606/108; 606/198; 623/1; 29/282
[58] Field of Search ..................................... 29/282, 283.5, 29/515, 516, 517, 715; 606/1, 108, 198; 623/1

[56] References Cited

U.S. PATENT DOCUMENTS

| | | |
|---|---|---|
| 696,289 | 3/1902 | Williams . |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,693,066 | 12/1997 | Rupp et al. .............................. 606/198 |
| 5,738,674 | 4/1998 | Williams et al. . |
| 5,746,764 | 5/1998 | Green et al. . |
| 5,782,855 | 7/1998 | Lau et al. ................................ 606/194 |
| 5,782,903 | 7/1998 | Wiktor ........................................ 623/1 |
| 5,783,227 | 7/1998 | Dunham . |
| 5,785,715 | 7/1998 | Schatz . |
| 5,810,838 | 9/1998 | Solar ...................................... 606/108 |
| 5,810,871 | 9/1998 | Tuckey et al. ........................... 606/198 |
| 5,810,873 | 9/1998 | Morales ................................... 606/198 |

(List continued on next page.)

FOREIGN PATENT DOCUMENTS

| | | |
|---|---|---|
| 0 826 346 | 3/1998 | European Pat. Off. . |
| 0 873 731 | 10/1998 | European Pat. Off. . |
| 159065 | 2/1921 | United Kingdom . |
| WO 98/14120 | 4/1998 | WIPO . |
| WO 98/19633 | 5/1998 | WIPO . |

OTHER PUBLICATIONS

U.S. application No. 08/795,335, filed Feb. 4, 1997.
U.S. application No. 08/837,771, filed Apr. 22, 1997.
U.S. application No. 08/089,936, filed Jul. 15, 1997.
U.S. application No. 08/962,632, filed Nov. 3, 1997.
*The eXTraordinary Stent*, C.R. Bard Brochure (Undated).

*Primary Examiner*—David P. Bryant
*Assistant Examiner*—Essama Omgba
*Attorney, Agent, or Firm*—Fulwider Patton Lee & Utecht, LLP

[57] ABSTRACT

A stent crimping tool for firmly and uniformly crimping a stent onto a balloon catheter. The stent crimping tool is constructed by curving and overlapping the ends of a flexible Mylar sheet and inserting the end portions through a thin slot of a rigid panel. The uncrimped stent and catheter assembly are placed within a cylindrical space formed by the curved and overlapping flexible sheet. A force is applied to the overlapping end portions to pull the flexible sheet through the slot thereby collapsing the cylindrical space and crimping the stent, held therein, onto the balloon. In another embodiment, the crimping tool is constructed from a mount having a grooved top with steeply sloped sides. The uncrimped catheter-stent assembly is placed on the mount and rests within the groove. A flexible sheet of Mylar is draped over the catheter-stent assembly and a downward force is applied to the end portions of the flexible sheet. This downward force places the flexible sheet in tension thereby compressing the catheter-stent assembly between it and the mount. Accordingly, the stent is crimped onto the balloon catheter.

13 Claims, 5 Drawing Sheets

U.S. PATENT DOCUMENTS

| | | | |
|---|---|---|---|
| 5,836,952 | 11/1998 | Davis et al. | |
| 5,893,852 | 4/1999 | Morales | 606/108 |
| 5,893,867 | 4/1999 | Bagaoisan et al. | 606/198 |
| 5,920,975 | 7/1999 | Morales | 29/282 |
| 5,931,851 | 8/1999 | Morales | 606/194 |
| 5,944,735 | 8/1999 | Green et al. | 606/194 |
| 5,947,993 | 9/1999 | Morales | 606/198 |
| 5,948,191 | 9/1999 | Solovay | 156/86 |
| 5,951,569 | 9/1999 | Tuckey et al. | 606/108 |
| 5,972,016 | 10/1999 | Morales | 606/198 |
| 5,974,652 | 11/1999 | Kimes et al. | 29/516 |
| 6,009,614 | 1/2000 | Morales | 29/516 |
| 6,024,737 | 2/2000 | Morales | 606/1 |
| 6,051,002 | 4/2000 | Morales | 606/108 |
| 6,063,092 | 5/2000 | Shin | 606/108 |
| 6,063,102 | 5/2000 | Morales | 606/198 |
| 6,074,381 | 6/2000 | Dinh et al. | 606/1 |

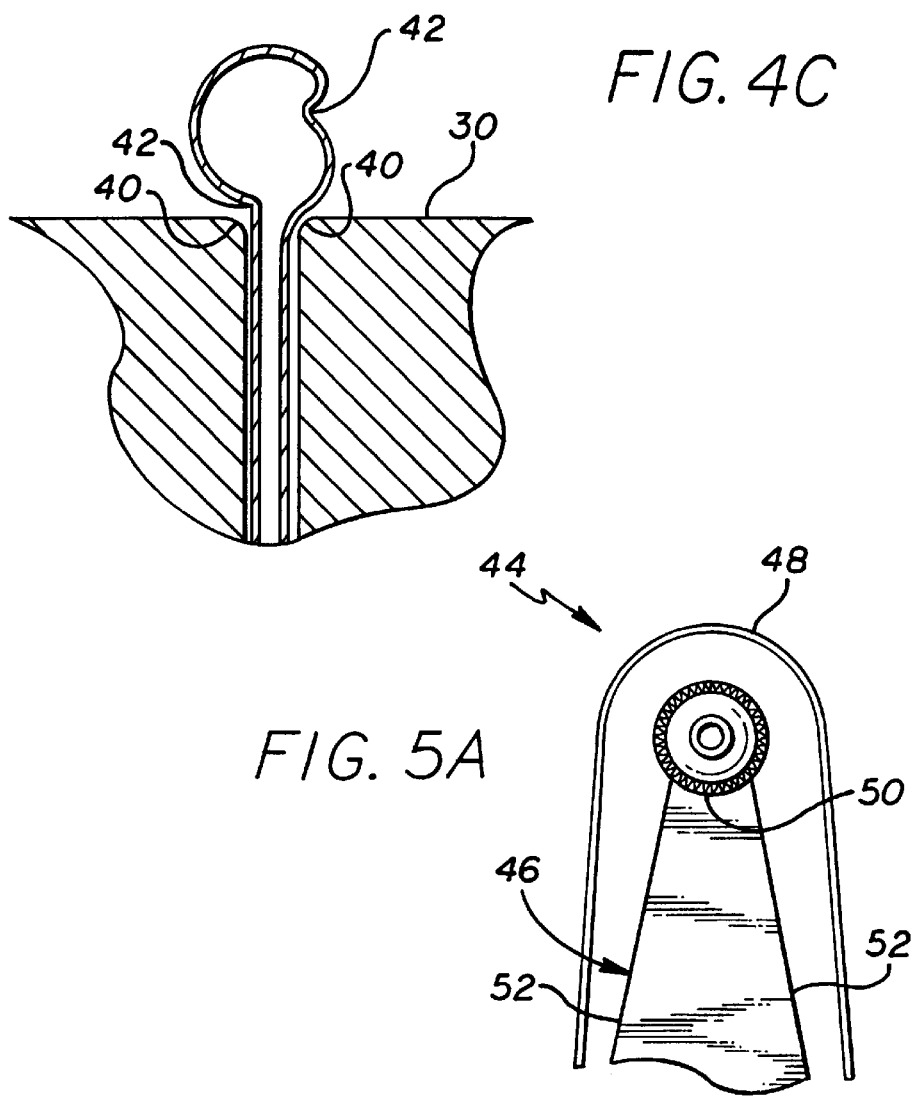
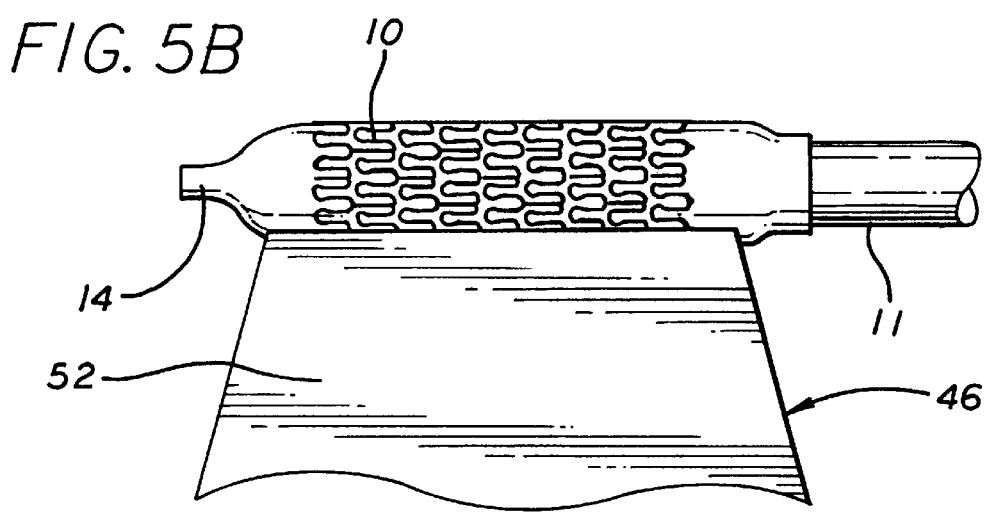

STENT CRIMPING TOOL AND METHOD OF USE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The bladder is inside a guide catheter. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by Johnson & Johnson and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel.

The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon. More precisely, the present invention is directed to a tool for crimping a stent onto a balloon catheter comprising a sheet of flexible material having a central portion and end portions, wherein the sheet is curved so that the end portions overlap. The present invention tool further comprises a rigid panel having a top side and a bottom side, and having a thin slot therethrough, a cylindrical space defined by the curved sheet, wherein the uncrimped stent is placed over the catheter to form a catheter-stent assembly, and wherein the catheter-stent assembly is disposed within the cylindrical space, wherein the overlapping end portions pass through the slot of the rigid panel so that the cylindrical space is disposed at the top side and the overlapping end portions are at the bottom side, and wherein the user pulls on the overlapping ends to collapse the sheet forming a significantly narrower cylindrical space thereby crimping the stent onto the catheter. In the preferred embodiment, the sheet of flexible material is made of Mylar. Further, to reduce friction between the Mylar sheet and the rigid panel, it is desirable to have a rounded edge around the thin slot.

To maximize the crimp on the stent to closely approximate the circle of the balloon catheter, the radius of curvature of the Mylar should not be less than the radius of curvature of the crimped stent. This demands that at the transition between the crimping portion of the Mylar and the part that is pulled through the thin slot, the Mylar must be plastically deformed. Indeed, the Mylar sheet undergoes a significant amount of stress at the point where it slides into the thin slot because, by design, it is expected to undergo a 180 degree turn.

If the Mylar sheet were preformed or prestressed, it might be better suited to achieving a near perfect circle. The perfect circle would translate to a more circular shape crimp on the stent. Also, the slot size could be reduced, which would allow an even closer approximation of the cylindrical shape over smaller sized balloons and stents.

Optionally, a rigid mandrel may be disposed within the guide wire lumen of the balloon catheter to help the structure maintain its shape during the crimping process. Thus, as the sheet squeezes down on the stent to crimp it to the balloon, the rigid mandrel resists the downward force and prevents the balloon from collapsing and losing its shape longitudinally.

In an alternative embodiment, the present invention stent crimping tool can be adapted to an actuator. The actuator may be spring loaded or pneumatically operated. For example, the user would initiate the actuator by moving a lever to release the spring which is biased to pull the overlapping end portions away from the panel thus tightly collapsing the cylindrical space thereby crimping the stent onto the balloon catheter. Alternatively, a piston disposed inside a fluid operated cylinder is connected to the overlapping end portions of the sheet. When actuated, the cylinder fills with fluid thereby displacing the piston and pulling the overlapping end portions away from the rigid panel thereby again collapsing the cylindrical space around the catheter-stent assembly and performing the stent crimping operation. The foregoing are examples of time saving, high force generating devices to be preferably incorporated into a high production procedure.

In an alternative embodiment, the present invention is directed to a tool for crimping a stent onto a catheter wherein the tool is mounted to a fixture, comprising a sheet of flexible material having a central portion and opposite end portions, a mount having a raised end grooved support surface with sloping sides, mounted to the fixture, wherein the uncrimped stent is mounted on the catheter and the catheter-stent assembly is placed on the grooved support surface which corresponds to the features of the stent, wherein the user curves the sheet to conform the central portion of the flexible sheet to the catheter-stent assembly, and so that the end portions overlie the sloping sides of the mount, and whereby the user pulls on the end portions to crimp the stent onto the catheter. In the preferred embodiment, the grooved support surface has a preferably semicircular cross-sectional shape. Furthermore, the sloping sides of the mount have low friction surfaces. Moreover, the sheet of flexible material is preferably made from Mylar.

During the stent crimping operation, the Mylar is pulled down over the mount, effectively squeezing the stent over the balloon portion of the catheter and the mount. By forcing at least one row of cells in the stent length to collapse, the stent should theoretically fit over the balloon perfectly, assuming correct sizing of the semicircular mount and assuming negligible friction between the stent and the Mylar sheet.

To insure secure and proper stent crimping, the Mylar should be released and the catheter-stent assembly rotated, and the foregoing process repeated. Again, an optional mandrel can be inserted into the guide wire lumen of the balloon catheter. During the repeated stent crimping process, the limit of deformation and crimping is reached when the radial forces encounter the mandrel, which resist further deformation and resultant decreases in the stent diameter.

The present invention tool is thus capable of homogeneously and precisely crimping a stent onto a balloon catheter. Such a crimping tool is highly useful to cardiologists, for example. Such physicians are constantly concerned with proper deployment of the stent within the patient that is desirable to have a consistently and reliably crimped stent. The present invention tool is further a time saver, because the stent crimping procedure can be performed efficiently and quickly. Indeed, these and other advantages of the present invention will become apparent from the following detailed description thereof when taken in conjunction with the accompanying exemplary drawings.

BRIEF DESCRIPTION OF THE DRAWINGS

FIGS. 4A, 4B, and 4C depict an alternative embodiment wherein the flexible sheet is creased or prestressed to create 90 degree angles that interact with the edges of the slot.

FIGS. 5A and 5B are front elevational and side elevational views, respectively, of an alternative embodiment stent crimping tool using a mount.

DETAILED DESCRIPTION OF THE PREFERRED EMBODIMENTS

Figure 1:
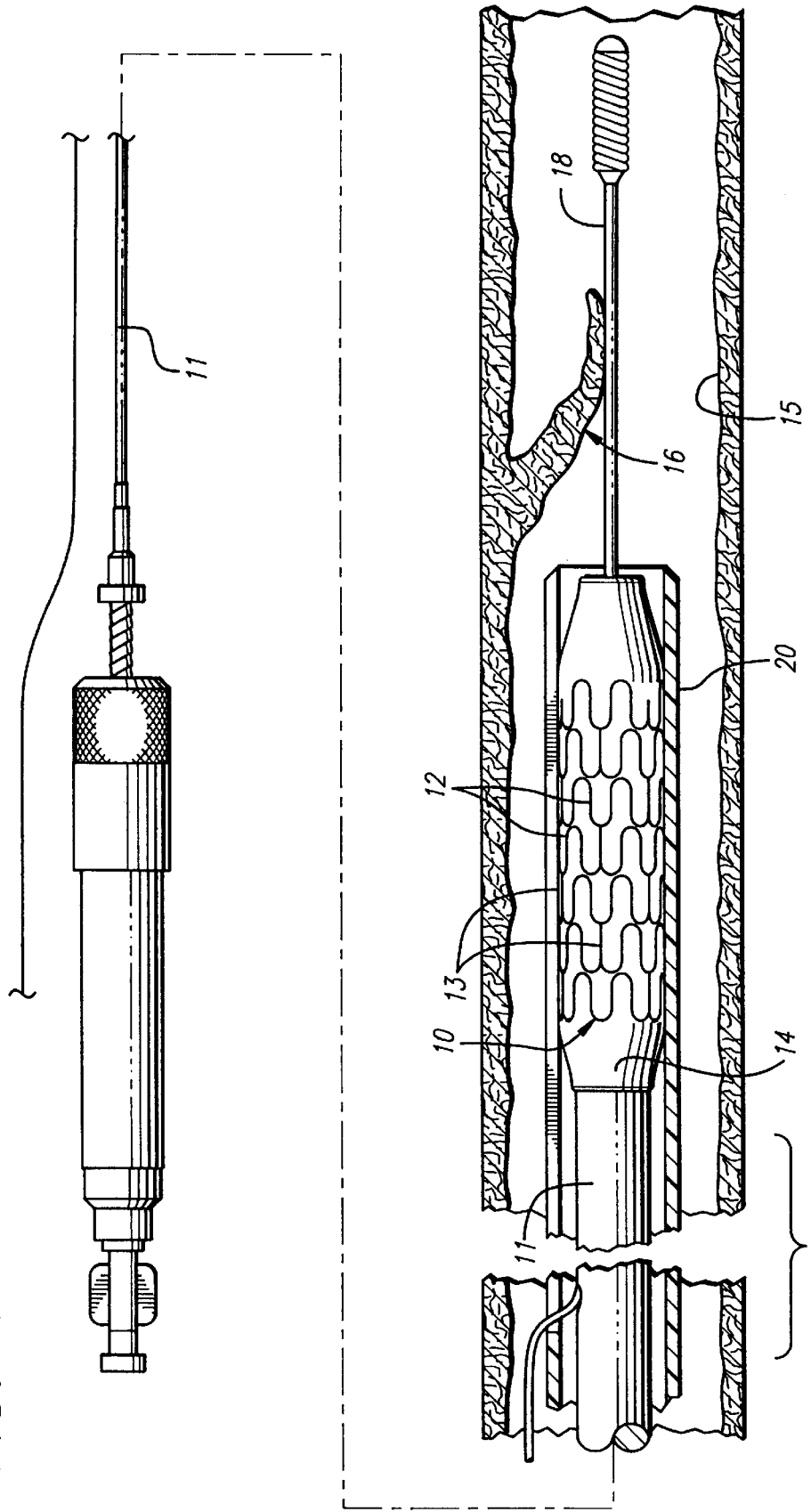
FIG. 1 is a side elevational view partially in section, depicting a stent that has been crimped onto a delivery catheter and disposed within a vessel.

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figure 2:
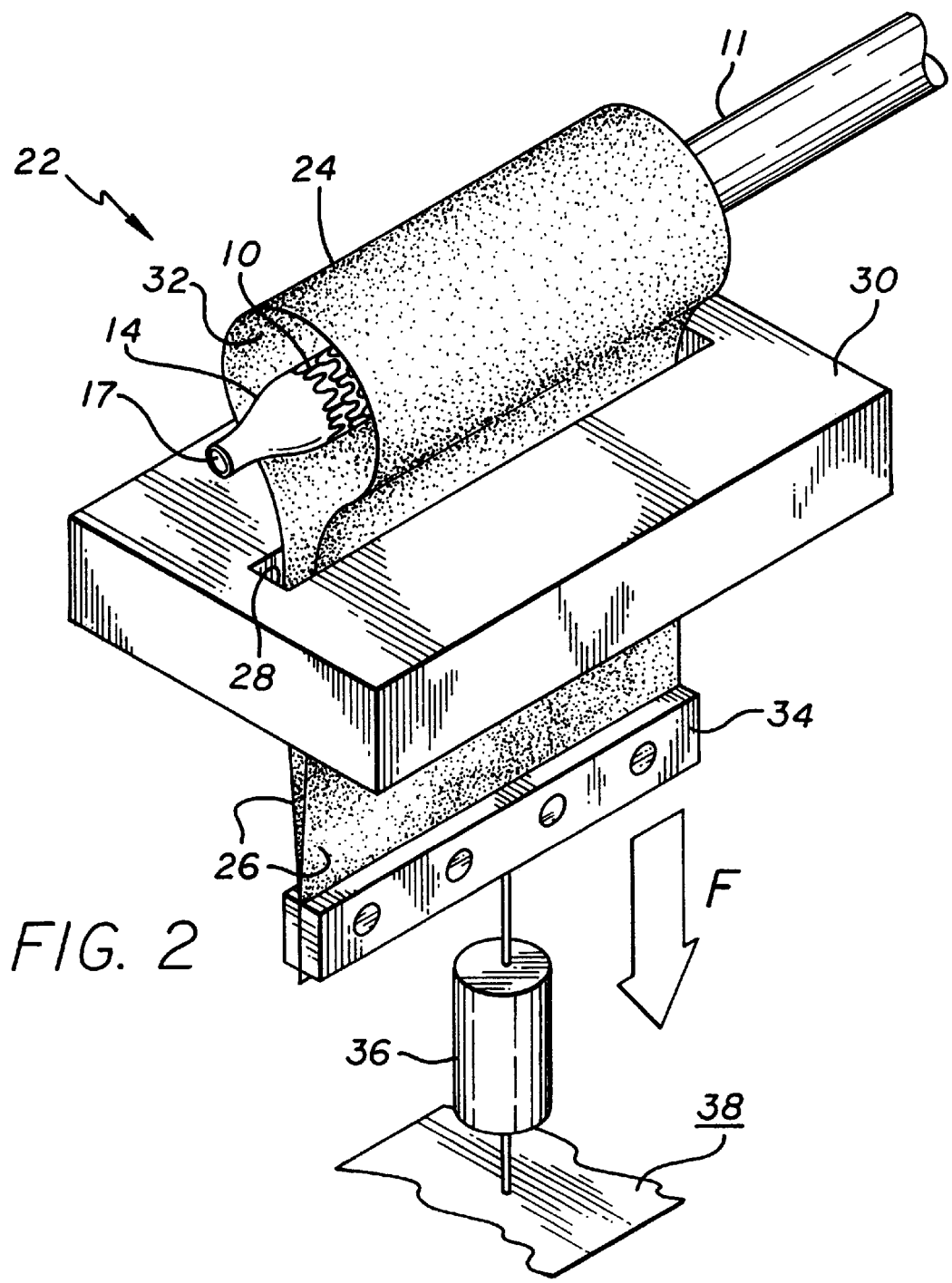
FIG. 2 is a perspective view of a preferred embodiment stent crimping tool showing the curved flexible sheet passing through a slot formed in a rigid panel.

FIG. 2 is a perspective view of a preferred embodiment of the present invention stent crimping tool 22. Specifically, the present invention is directed to tool 22 for crimping intravascular stent 10 onto balloon 14 of delivery catheter 11. In a preferred embodiment, stent crimping tool 22 includes sheet 24 that is made from a flexible material, such as Mylar. Flexible sheet 24 is curved and folded over so that end portions 26 thereof overlap as shown in the perspective view of FIG. 2. As part of the invention, end portions 26 of flexible sheet 24 are designed to pass through thin slot 28 formed in rigid panel 30. Preferably, rigid panel 30 is locked or mounted to a stationary work bench, fixture, or the like. The mounting hardware has been omitted from FIG. 2 for the sake of clarity.

As seen in FIG. 2, after uncrimped stent 10 is loaded onto balloon 14 of delivery catheter 11, the catheter-stent assembly is placed within cylindrical space 32 formed by curving and overlapping flexible sheet 24. End portions 26 are held together by optional clamp 34, which is used to apply a downward force represented by arrow F. This downward force F pulls flexible sheet 24 through thin slot 28 and simultaneously collapses cylindrical space 32. Continued downward force F on end portion 26 stretches flexible sheet 24 taut around the catheter-stent assembly. Because of its size relative to thin slot 28, the catheter-stent assembly cannot pass through thin slot 28 while flexible sheet 24 can slide therethrough. This is therefore the preferred mechanism used to crimp stent 10 onto balloon 14.

Optionally, a rigid mandrel (not shown) may be disposed within guide wire lumen 17 of delivery catheter 11 to help the structure maintain its shape during the crimping process. Thus, as flexible sheet 24 squeezes down on stent 10 to crimp it onto balloon 14, the rigid mandrel resists the downward force and prevents balloon 14 from collapsing completely and losing its shape.

In addition, the present invention crimp stenting tool can be adapted for use with an actuator. For example, actuator 36 is anchored to ground 38 and can be embodied in a spring or a pneumatically operated piston within a cylinder. Actuator 36 can be manually operated, lever operated, pneumatically operated, or triggered by a similar technology known in the art in order to generate the downward force F. Primarily, actuator 36 would be used as a time saving measure for high cyclic rates in a production line for example. Moreover, a machine generated downward force would be uniform and controlled so that very precise crimping of stent 10 can be achieved.

Figure 3:
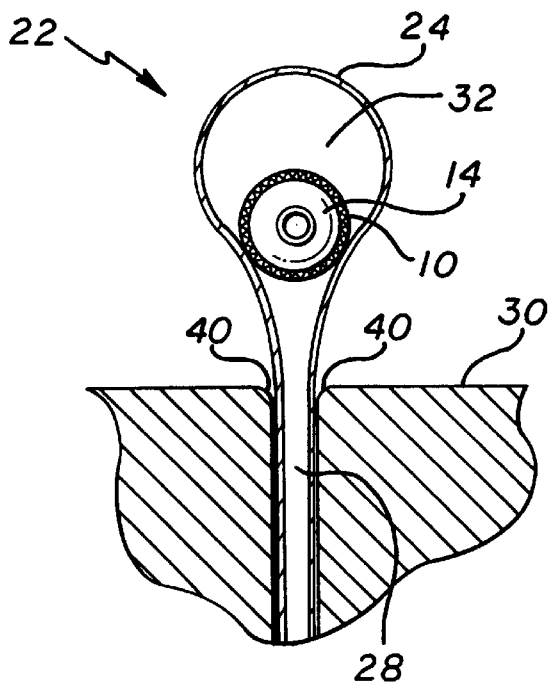
FIG. 3 is a side elevational view of the embodiment shown in FIG. 2.

FIG. 3 provides a front elevational view of the present invention stent crimping tool 22. In the instant of time shown here, the catheter-stent assembly has been positioned within cylindrical space 32 of curved flexible sheet 24 similar to the depiction in FIG. 2. As best seen in FIG. 3, rigid panel 30 is represented in a cross-section to best illustrate thin slot 28 with rounded edges 40. Rounded edges 40 are preferable because as tension is applied to flexible sheet 24 to draw the material through thin slot 28, flexible sheet 24 assumes a tear drop shape that does not conform stent 10 to balloon 14 very well. Rounded edges 40 therefore reduce frictional drag on the movement of flexible sheet 24 through thin slot 28, and further insures a tighter crimp as flexible sheet 24 pulls the catheter-stent assembly against rounded edges 40.

Figure 4A:
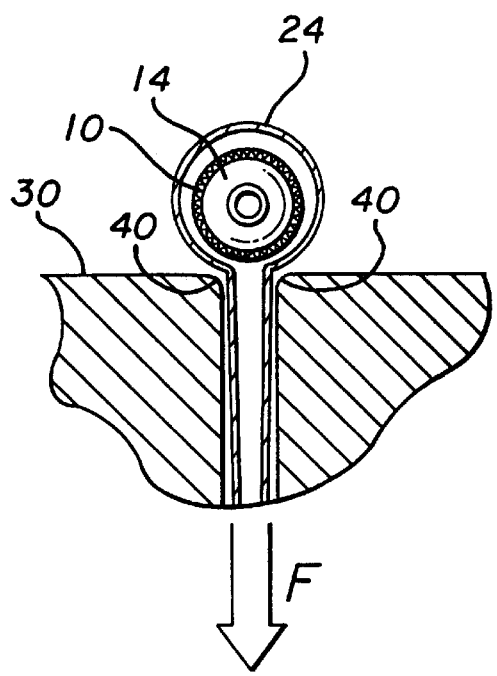
Figure 4B:
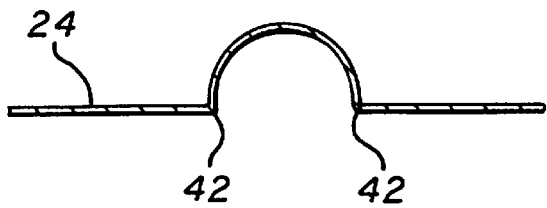

Ideally, to maximize the crimp of stent 10 onto balloon 14, the radius of curvature of cylindrical space 32 formed by flexible sheet 24 should not be less than or greater than but exactly the radius of the crimped stent. This demands that at the transition between the crimping portion of flexible sheet 24 and the portion thereof that is pulled through thin slot 28, flexible sheet 24 is plastically deformed. Indeed, flexible sheet 24 undergoes a significant amount of stress at the point where it slides into thin slot 28 because, by design, it is expected to undergo a 90 degree turn. This is illustrated in the front elevational view of FIG. 4A. If flexible sheet 24 were preformed (i.e., prestressed) as seen in the front elevational view of FIG. 4B, it is possible to achieve a near perfect circle surrounding the catheter-stent assembly resulting in a symmetrical crimp as shown in FIG. 4A. To be sure, FIG. 4C provides a front elevational view of a preformed or prestressed flexible sheet 24 which is shown being pulled through thin slot 28 of rigid panel 30. Because the process is not complete and flexible sheet 24 has not been pulled through thin slot 28 sufficiently to remove slack, 90 degree turn kinks 42 do not coincide with rounded edges 40.

FIGS. 5–8 depict an alternative embodiment of the present invention. FIGS. 5A and 5B provide a front elevational and a side elevational view of an alternative embodiment of the present invention stent crimping tool 44. In this preferred embodiment, stent crimping tool 44 includes mount 46 operating in conjunction with flexible sheet 48. In the front elevational view of FIG. 5A, the present invention is shown in connection with an uncrimped catheter-stent assembly placed upon mount 46. To insure stability, mount 46 preferably includes a grooved surface to help center the catheter-stent assembly thereon. In particular, groove 50 preferably has a radius that approximates the catheter-stent assembly.

FIG. 5B is a side elevational view wherein flexible sheet 48 has been omitted to expose placement of the catheter-stent assembly on mount 46. In this view, it can be seen that stent 10 has already been loaded onto balloon 14 of catheter 11. In the preferred embodiment, mount 46 generally has a lengthwise dimension approximating the length of stent 10. Mount 46 is situated on a work surface so that it is stable and immobile during the crimping process.

Mount 46 can be fashioned from a rigid material known in the art. Importantly, mount 46 has steeply sloped side walls 52 to minimize frictional drag and interference with movement of flexible sheet 48 during the crimping process.

Figure 6:
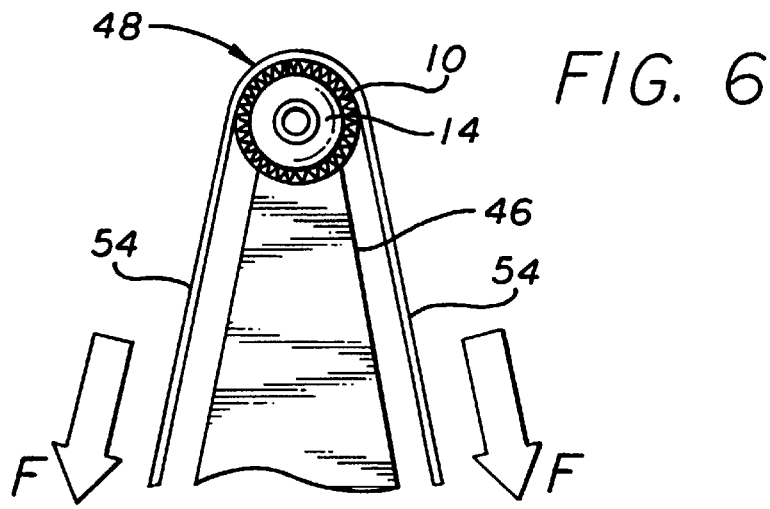
FIG. 6 is a front elevational view of the alternative embodiment shown in FIG. 5A, wherein the stent is undergoing the crimping procedure.
Figure 7:
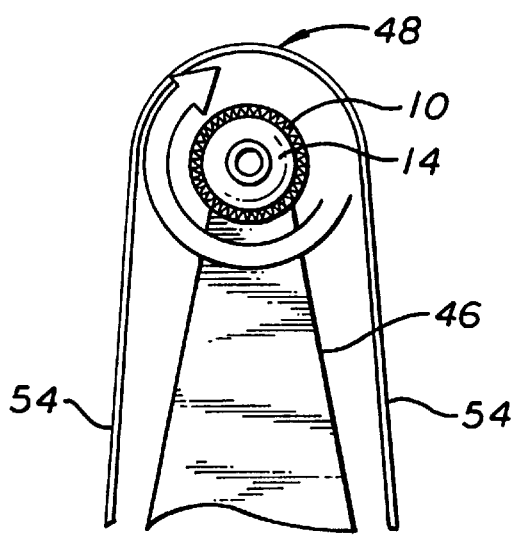
FIG. 7 is a front elevational view of the embodiment shown in FIG. 5A, wherein the pressure on the flexible sheet has been released to rotate the catheter-stent assembly.
Figure 8:
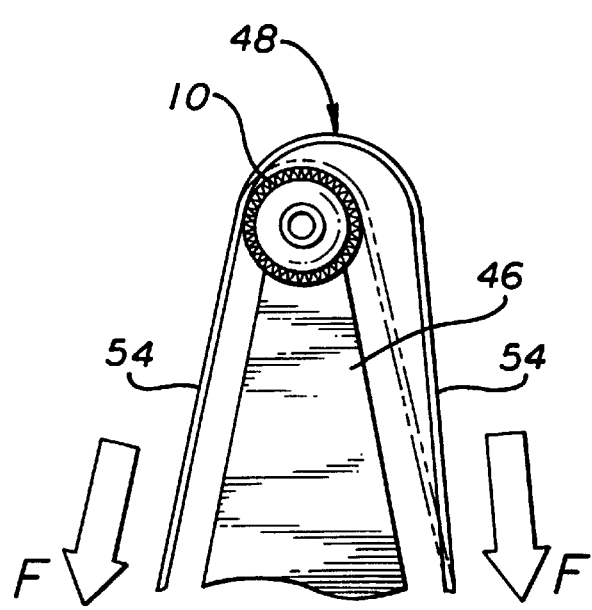
FIG. 8 is a front elevational view of the alternative embodiment shown in FIG. 5A wherein the flexible sheet is pulled downward to continue the crimping procedure.

FIGS. 6–8 illustrate use of the present invention stent crimping tool 44. FIG. 6 provides a front elevational view of stent crimping tool 44 when a downward force is exerted at end portions 54 of flexible sheet 48. The downward force is represented by arrows labeled F. This force places flexible sheet 48 in tension and compresses the catheter-stent assembly between flexible sheet 48 and mount 46. As seen in the previous exemplary embodiment, the present invention may be used with an optional rigid mandrel that is inserted into a guide wire lumen of balloon 14 to provide internal support during the crimping process.

In FIG. 7, the downward force and tension in flexible sheet 48 have been removed; this state is depicted with flexible sheet 48 having slack. In this state, it is possible to rotate the catheter-stent assembly to reorient the parts before undergoing the next crimping step. To this end, FIG. 8 shows downward force F being reapplied to end portions 54 of flexible sheet 48 to again resume compressing the catheter-stent assembly between flexible sheet 48 and mount 46. The steps shown in FIGS. 6–8 are repeated until stent 10 is firmly crimped onto balloon 14.

As seen with the previous embodiment of the present invention, it is possible to mechanize or automate this process by use of actuators discussed earlier. Once the process is complete, the downward force F is removed to remove the tension from flexible sheet 48. The crimped catheter-stent assembly can then be removed from the crimping tool 44.

In the preferred embodiment, groove 50 has a cradle or semicircular cross-sectional shape to support the catheter-stent assembly during the crimping process. Other cross-sectional shapes are contemplated, and may be useful for various purposes or to accommodate varying stent profiles. Groove 50 may be optionally coated, covered, or include other surface features. Such surface features include optional ribs, contours, bumps, indentations, and the like to accommodate the features of the catheter-stent assembly, to provide support and stability, or to achieve frictional contact with the catheter-stent assembly to minimize twisting.

Mount 46 is preferably held inside another enclosure (not shown) for correct alignment of stent 10 and balloon 14. Again, as mentioned earlier, flexible sheet 48 is preferably made from Mylar or the like and should drape over side walls 52 of mount 46. Correct sizing between stent 10 and flexible sheet 48 insures a perfect fit of stent 10 over balloon 14. This is assuming negligible friction between stent 10 and flexible sheet 48. In either the present embodiment as with the earlier embodiment, the catheter-stent assembly can be rotated during the crimping process to insure a symmetrical, homogenous and even crimping of the stent to the balloon catheter.

The present invention is sterilized and intended to be used in a cath lab by a trained technician or cardiologist. More precisely, as is appreciated by those skilled in the art, the present invention crimping tool 22 is designed both for single use applications in a cath lab by a physician, or for multiple use applications in a sterile environment in a high volume manufacturing facility. In such a manufacturing facility where sterile conditions exist, stent crimping tool 22 can be used repeatedly to crimp stents onto balloons until the mechanism wears out. Thus, repeated uses of the present invention are contemplated for controlled, sterile, environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A tool for crimping a stent on to a balloon catheter by a user, comprising:
    a sheet of flexible material having a central portion and end portions, wherein the sheet is curved so that the end portions overlap;
    a rigid panel having a top side and a bottom side, and having a thin slot therethrough;
    a cylindrical space defined by the curved sheet, wherein an uncrimped stent is placed over the catheter to form a catheter-stent assembly, and wherein the catheter-stent assembly is disposed within the cylindrical space;
    wherein the overlapping end portions pass through the slot of the rigid panel so that the cylindrical space is disposed at the top side and the overlapping end portions are at the bottom side; and
    wherein the user pulls on the overlapping ends to collapse the sheet forming the cylindrical space thereby crimping the stent onto the catheter.

2. The crimping tool of claim 1, wherein the sheet of flexible material includes a polymer.

3. The crimping tool of claim 1, wherein the sheet of flexible material includes polyethylene terephthalate.

4. The crimping tool of claim 1, wherein the thin slot has a rounded edge.

5. The crimping tool of claim 1, wherein the rigid panel includes a low friction surface area proximate to the thin slot.

6. The crimping tool of claim 1, wherein a mandrel is disposed within a guide wire lumen of the catheter.

7. The crimping tool of claim 1, wherein the overlapping ends are connected to a spring biased to pull the overlapping ends away from the rigid panel.

8. The crimping tool of claim 1, wherein the overlapping ends are connected to a pressurized piston contained in a cylinder that pulls the overlapping ends away from the rigid panel when a fluid is injected into the cylinder.

9. A method for crimping a stent on to a catheter, comprising the steps of:

providing a sheet of flexible material having a central portion and opposed end portions;

providing a rigid panel having a first side and an opposed second side, and having a thin slot therethrough;

folding the sheet to curve the central portion to define a cylindrical space and to overlap the opposed end portions;

placing the stent over the catheter to form a catheter-stent assembly;

inserting the catheter-stent assembly into the cylindrical space;

passing the overlapping end portions through the thin slot from the first side toward the second side so that the central portion is adjacent the first side and the overlapping end portions are adjacent the second side;

translating the rigid panel along the sheet toward the cylindrical space; and collapsing the cylindrical space to crimp the stent onto the catheter.

10. The method of claim 9, wherein the sheet of flexible material includes polyethylene terephthalate.

11. The method of claim 9, wherein the edge of the thin slot is rounded.

12. The method of claim 9, wherein the step of folding the sheet provides a radius of curvature of the sheet that is greater than a radius of curvature of the crimped stent.

13. The method of claim 9, wherein the method further comprises the step of rotating the catheter-stent assembly.

* * * * *